United States Patent
Koolbergen et al.

(10) Patent No.: US 10,195,337 B2
(45) Date of Patent: Feb. 5, 2019

(54) SYSTEM FOR FLUSHING A PERICARDIAL CAVITY

(71) Applicant: ACADEMISCH MEDISCH CENTRUM, Amsterdam (NL)

(72) Inventors: David Robert Koolbergen, Amsterdam (NL); Johan Samuel Jakob Manshanden, Amsterdam (NL)

(73) Assignee: ACADEMISCH MEDISCH CENTRUM, Amsterdam (NL)

( * ) Notice: Subject to any disclaimer, the term of this patent is extended or adjusted under 35 U.S.C. 154(b) by 248 days.

(21) Appl. No.: 15/103,285

(22) PCT Filed: Dec. 15, 2014

(86) PCT No.: PCT/EP2014/077823
§ 371 (c)(1),
(2) Date: Jun. 9, 2016

(87) PCT Pub. No.: WO2015/086857
PCT Pub. Date: Jun. 18, 2015

(65) Prior Publication Data
US 2016/0331888 A1    Nov. 17, 2016

(30) Foreign Application Priority Data
Dec. 13, 2013  (EP) .................................... 13197090

(51) Int. Cl.
*A61M 3/02*  (2006.01)
*A61M 1/00*  (2006.01)

(52) U.S. Cl.
CPC .......... *A61M 3/0258* (2013.01); *A61M 1/006* (2014.02); *A61M 1/0025* (2014.02);
(Continued)

(58) Field of Classification Search
CPC .. A61M 3/0258; A61M 1/0025; A61M 1/006; A61M 1/0058; A61M 2205/502;
(Continued)

(56) References Cited

U.S. PATENT DOCUMENTS 4,773,423 A   9/1988  Hakky
5,586,973 A   12/1996 Lemaire et al.
(Continued)

FOREIGN PATENT DOCUMENTS

DE      41 02 843 C1     5/1992
WO      92/18049 A1      10/1992
(Continued)

OTHER PUBLICATIONS

"Re-Exploration for Bleeding or Tamponade after Cardiac Surgery: Impact of Timing and Indication on Outcome." Haneya A et al., Thorac Cardiovasc Surg. Sep. 29, 2014.

*Primary Examiner* — Amber Stiles
(74) *Attorney, Agent, or Firm* — Maschoff Brennan

(57) ABSTRACT

The invention provides a flushing system (1) configured to flush the pericardial cavity (PC) of a patient, wherein the system comprises: an infusion liquid outlet (4) to connect a first tube (20) having an infusion liquid lumen to guide a flow of infusion liquid from the system to the pericardial cavity, and an effusion liquid inlet (6) to connect to a second tube (21) having an effusion liquid lumen to guide the effusion liquid flow from the pericardial cavity to the system, a flow rate control system to control the flow rate of the infusion liquid flow at the infusion liquid outlet (4) on the basis of multiple sensor signals, wherein the flow rate control system comprises: a control unit (5) to provide a control signal on the basis of the sensor signals, and a pump device (3) to pump infusion liquid to the infusion liquid outlet (4) at an infusion liquid flow rate, wherein the infusion liquid flow
(Continued)

rate is adjustable by the control signal of the control unit (5) and wherein the sensor signals registered by the control unit (5) comprise: an infusion liquid signal representative for the infusion liquid flow to the pericardial cavity, an effusion liquid signal representative for the effusion liquid flow rate from the pericardial cavity, a blood volume signal generated by a hematocrit sensor (12) representative for a blood loss flow rate in the effusion liquid from the pericardial cavity, and a pressure control signal representative for the pressure in the pericardial cavity generated by a pressure sensor positioned inside or in connection with the first tube (20), the second tube (21) or the pericardial cavity. The invention also provides a method of monitoring the blood loss volume or flow rate from the pericardium based on multiple sensor signals as well as, a method of treatment of postoperative cardiac patients in order to reduce the risk of cardiac tamponade, reduce post-operative blood loss and reduce the accumulation of blood and clots in the pericardial cavity, wherein the pericardial cavity of the patient is flushed with a flushing system according to the invention.

21 Claims, 3 Drawing Sheets

(52) U.S. Cl.
CPC ... *A61M 1/0058* (2013.01); *A61M 2205/3334* (2013.01); *A61M 2205/3344* (2013.01); *A61M 2205/3368* (2013.01); *A61M 2205/36* (2013.01); *A61M 2205/50* (2013.01); *A61M 2205/502* (2013.01); *A61M 2210/101* (2013.01); *A61M 2210/122* (2013.01); *A61M 2230/005* (2013.01); *A61M 2230/207* (2013.01)

(58) Field of Classification Search
CPC ........ A61M 2230/005; A61M 2205/36; A61M 2205/3344; A61M 2205/3368; A61M 2230/207; A61M 2210/101; A61M 2205/50; A61M 2205/334; A61M 2205/3334; A61M 2210/122
See application file for complete search history.

(56) References Cited

U.S. PATENT DOCUMENTS

| 5,709,670 | A | 1/1998 | Vancaillie et al. |
| 5,814,009 | A | 9/1998 | Wheatman |
| 2010/0228222 | A1 | 9/2010 | Williams et al. |

FOREIGN PATENT DOCUMENTS

| WO | WO 9218049 A1 * | 10/1992 | ............ A61B 1/12 |
| WO | 02/07798 A2 | 1/2002 | |
| WO | 2008/043067 A2 | 4/2008 | |

* cited by examiner

SYSTEM FOR FLUSHING A PERICARDIAL CAVITY

TECHNICAL FIELD

The present invention relates to a flushing system configured for postoperative flushing of the pericardial cavity of a patient. The present invention in particular relates to a flushing system for flushing the pericardial cavity of a patient as a postoperative treatment in order to reduce the risk of cardiac tamponade, reduce postoperative blood loss and reduce the accumulation of blood and clots in the pericardial cavity.

BACKGROUND

Excessive postoperative blood loss which might amount to more than 2 L per 24 hours or more than 200 mL per hour is a known complication of cardiac surgery. Reoperation/re-exploration for bleeding is a strong independent risk factor for adverse outcome following cardiac surgery with higher mortality and morbidity rates. In addition, postoperative bleeding requiring multiple transfusions and surgical re-exploration is associated with higher costs, increased sternal wound infection, and transfusion-related infection.

To evacuate blood from the pericardial cavity—and if necessary pleural cavities,—chest tubes are left postoperative. However, when blood loss is excessive or when clots start to develop more rapidly, the drains often fail in their function to evacuate all accumulated blood. Stasis of clots and blood in the pericardial (and/or pleural) cavity may lead to high fibrinolytic activity, maintenance of blood loss and in some cases to cardiac tamponade. In case of acute cardiac tamponade the pressure in the pericardial space exceeds the filling pressure of the heart, leading to collapse of the thinwalled right atrium and consequently to inflow obstruction of blood towards the heart. This will lead to low cardiac output and if not detected and treated early eventually to death. In case of cardiac tamponade only emergency reoperation can save the patient although even in this group mortality and morbidity rates are higher. This specially applies to delayed reoperation, indicating that early detection is essential.

In current clinical practice there are no special measures to prevent cardiac tamponade other than leaving the normal pericardial/wound drains and be very alert for cardiac tamponade to occur. The monitoring that is used is blood pressure and central venous pressure (CVP). When a blood pressure drop is observed it is actually too late because the tamponade is already there and the patient will probably not be stable enough to return to the OR. Central venous pressure is measured in the right atrium and is a reflection of the intrapericardial pressure because the right atrium is very thin walled. But it is indirect and often not reliable because it depends on the patient's position, the transducer position and often the line is used for infusion of medication. So a continuously measured intrapericardial pressure would be a great improvement of the patient's safety.

The clinical significance of cardiac tamponade and early detection and timely re-intervention for bleeding is discussed by Haneya A et al. Re-Exploration for Bleeding or Tamponade after Cardiac Surgery: Impact of Timing and Indication on Outcome. Thorac Cardiovasc Surg. 2014 Sep. 29. The citations below are illustrative for the serious consequences of an acute cardiac tamponade.

"Objectives: Re-exploration after cardiac surgery remains a frequent complication with adverse outcomes. The aim of this study was to evaluate the impact of timing and indication of re-exploration on outcome.

Methods: A retrospective, observational study on a cohort of 209 patients, who underwent re-exploration after cardiac surgery between January 2005 and December 2011, was performed. The cohort was matched for age, gender, and procedure with patients who were not re-explored during the same period.

Results: The intraoperative and postoperative transfusion requirements were higher in the re-exploration group ($p<0.01$). Patients in the re-exploration group had significantly higher incidences of postoperative acute renal injury (10.0 vs. 3.3%), sternal wound (9.1 vs. 2.4%) and pulmonary (13.4 vs. 4.3%) infections, longer ventilation time (22 [range, 14-52] vs. 12 [range, 9-16] hours) and intensive care unit stay (5 [range, 3-7] vs. 2 [range, 2-4] days), and higher mortality rate (9.6 vs. 3.3%). However, the multivariate logistic regression analysis demonstrated that not the re-exploration itself, but the deleterious effects of re-exploration (blood loss and transfusion requirement) were independent risk factors for mortality. Mortality was 5.3% for patients who were re-explored within the first 12 hours and 20.3% for patients who were re-explored after 12 hours ($p=0.003$). Mortality was 3.6% for patients with bleeding and 31.4% for patients with cardiac tamponade for indication of re-exploration ($p<0.001$).

Conclusions: This study indicates that re-exploration after cardiac surgery is associated with increased mortality and morbidity. Patients with delayed re-exploration and suffering from cardiac tamponade have adverse outcome."

It is an object of the invention to provide a system and/or method that reduces one or more of the above risks or complications, in particular caused by post-operative blood loss from the pericardial cavity, and to prevent or at least provide an early detection of an increased threat of acute cardiac tamponade This is achieved by a flushing system as defined in claim 1 which is based on a unique combination of sensors each providing signals to a control unit which controls the flow rate of the infusion liquid to the pericardial cavity in a patient.

Flushing systems for flushing various body cavities during and/or an operation are known in the art. The flushing or irrigation of body cavities was introduced as a necessity during endoscopic surgery (e.g. hysterectomy or operations on the bladder) in order to ensure the surgeon's clear view of the operation site ,but also to remove collected particles of tissue, blood and fragments form the interior of the body cavity. This made "fluid management" of the irrigation fluid during operations an obvious desideratum, both for the securing a continuous flow of irrigation fluid and for quantifying the blood loss during the operation Thus, WO 02/07798 A2 describes a system for securing continuous flow during an operation. The system is mainly concerned with urological endoscopic operations where large volumes of fluid are necessary to continuously flush the operation site in order to maintain visibility during the operation and post-operational flushing of the operated body cavity is desired. The system has a plurality of containers and sensors and closure devices to ensure a switch from an empty to a full container and means for measuring the volume of fluid from the operation site and compare the fluid delivered with fluid removed during and after the operation e.g by use of suitable volume sensors This balance of fluids is necessary because of a special problem related to endoscopic operations, viz. the risk of absorption of flushing liquid in the patient's body. An opacity meter may be used to measure the clarity of the fluids removed, so as to determine whether there is still bleeding. Also, such a system cannot be used to meet the special requirements relating to post-operational pericardial flushing with risk of provoking a cardiac tamponade.

The pericardial flushing device is specifically designed to clean the pericardial space after cardiac surgery. The system works by flushing the pericardial cavity with a saline (or other) solution, thereby lowering the viscosity and the hematocrit value of the blood present in the cavity and at the same time preventing the formation of larger clots. Cleaning the pericardial space by flushing will prevent clogging of the chest drains and the consequent accumulation of blood and clots in the pericardial space. This will lead to less postoperative bleeding and diminish the risk for provoking an acute cardiac tamponade. According to the invention, this is achieved by means of unique use of volume, hematocrit and pressure sensors in the flushing system as further described below.

When the outflow drains clog partially or completely despite the flushing device, the infused liquid volume is added to the accumulating blood in the pericardium which will lead to a more rapid increase of the liquid volume and pressure in that particular space. Also for this reason early detection of (increased threat of) cardiac tamponade by means of a pressure sensor is essential so that a signal can be given to a control unit that the infusion of liquid should be stopped immediately.

Also, by diluting the pericardial blood effusion with saline (or other solutions), the exact amount of blood loss is unclear. Knowing exact amount of blood loss is essential in postoperative decision-making with as regards to the needs for reoperation/re-exploration of the pericardial space. In table 5-6 the criteria for reoperation are given (from Cardiac Surgery textbook by John W. Kirklin and Brian G. Barratt-Boyes, second edtion 1993).

TABLE 5-6

ENERAL CONSIDERATIONS
Chest Drainage Criteria for Reoperation

| Preoperative Weight | Chest Drainage Indicating Reoperation | | | | |
|---|---|---|---|---|---|
| | Hourly Amount (ml · h$^{-1}$) No. of Successive Hours[a] | | | Total Amount (ml) Hour No.[b] | |
| (kg) | 1 | 2 | 3 | 4 | 5 |
| 5.0 | 70 | 60 | 50 | 120 | 130 |
| 6.0 | 70 | 60 | 50 | 130 | 155 |
| 7.0 | 70 | 60 | 50 | 150 | 180 |
| 8.0 | 90 | 70 | 50 | 175 | 200 |
| 9.0 | 90 | 80 | 60 | 195 | 230 |
| 10.0 | 100 | 90 | 65 | 220 | 260 |
| 12.0 | 130 | 100 | 80 | 260 | 300 |
| 14.0 | 150 | 120 | 90 | 300 | 360 |
| 16.0 | 170 | 140 | 100 | 350 | 400 |
| 18.0 | 195 | 150 | 120 | 390 | 460 |
| 20.0 | 200 | 175 | 130 | 450 | 520 |
| 25.0 | 270 | 220 | 160 | 540 | 650 |
| 30.0 | 325 | 260 | 195 | 650 | 770 |
| 35.0 | 380 | 300 | 230 | 760 | 900 |
| 40.0 | 430 | 350 | 260 | 800 | 1,035 |
| 45.0 | 500 | 400 | 300 | 975 | 1,150 |
| 50.0 | 500 | 400 | 300 | 1,000 | 1,200 |

[a]Reoperation is advisable if the patient has bled the amount indicated in any 1 hour (column 1), the lesser amount in column 2 during each of any 2 successive hours, or the still smaller amount (column 3) in each of any 3 successive hours.
[b]Reoperation is advisable, if by the end of the fourth or fifth postoperative hour, the patient has bled in total the amount indicated.

The criteria for patients of 50 kg apply for all adult patients with a body weight of more than 50 kg. From the table one can derive that in the decision-making process not only the absolute amount of blood loss, but also the trend is important. A relatively high amount of blood loss can still be acceptable as long as the trend is downwards.

Following from this, it is important to know the exact amount of blood loss per hour, the trend in blood loss and the total amount of blood loss over the whole postoperative period. This will enable the medical staff to to make a well-founded and timely decision whether or not to take the patient back to the operation room for re-exploration of the wound area.

This will also contribute to the clinical decision whether or not to give a blood transfusion. This in itself will also affect the patients' outcome. Not giving a blood transfusion when necessary will worsen the outcome and on the other side, giving a blood transfusion when not really necessary will do the same.

Transfusing an anaemic patient will improve the outcome. Blood transfusion has a clearly defined role in the management of haemorrhagic shock and is presumably beneficial in situations where a critically low hematocrit is contributing to a state of oxygen-supply dependency. A number of studies have demonstrated that low hemoglobin (Hb) concentrations and decreased oxygen delivery increase mortality. Thus it was found that patients who had a lower hematocrit during surgery were associated with a higher risk of in-hospital mortality. The potential benefits are, however, countered by many transfusion-associated complications: the risk of transfusion-associated lung injury, transfusion associated immunomodulation, transfusion-related circulatory overload,) and cellular hypoxia. Blood transfusions have also been linked to postoperative renal dysfunction, pneumonia, wound infections) and severe sepsis.) There have been several recent well-designed randomized control trials in patients undergoing cardiac surgery showing a significant association of transfusion with increased short- and long-term postoperative mortality of 66%; morbidity and healthcare costs.

SUMMARY OF THE INVENTION

The invention provides a flushing system configured to flush the pericardial cavity of a patient, wherein the system comprises:
an infusion liquid outlet to connect a first tube having an infusion liquid lumen to guide the infusion liquid flow from the system to the pericardial cavity, and
an effusion liquid inlet to connect to a second tube having an effusion liquid lumen to guide the effusion liquid flow from the pericardial cavity to the system
a flow rate control system to control the flow rate of the infusion liquid flow at the infusion liquid outlet on the basis of multiple sensor signals, wherein the flow rate control system comprises:
a control unit to provide a control signal on the basis of the sensor signals, and
a pump device to pump infusion liquid to the infusion liquid outlet at an infusion liquid flow rate, wherein the infusion liquid flow rate is adjustable by the control signal of the control unit
and wherein the sensor signals registered by the control unit comprise
an infusion liquid signal representative for the infusion liquid flow rate to the pericardial cavity,
an effusion liquid signal representative for the effusion liquid flow rate from the pericardial cavity, a blood volume signal generated by a hematocrit sensor representative for a blood loss flow rate in the effusion liquid from the pericardial cavity, and a pressure control signal representative for the pressure in the pericardial cavity generated by a pressure sensor positioned inside or in connection with the first tube, the second tube or the pericardial cavity The flushing system is configured to provide a flow of infusion liquid towards the pericardial cavity, whereby the flow rate of the infusion liquid flow may be controlled by the control unit of the flushing system in dependence of the volume of effusion liquid flowing out of the pericardial cavity, the actual blood loss in this effusion liquid flow which is calculated from the outflow volume and hematocrit sensor values, and the pressure in the pericardial cavity By adapting the flow rate of infusion liquid to these parameters, the evacuation of blood and clots from the pericardial cavity can be enhanced without pumping an excessive amount of infusion liquid into the pericardial cavity and possibly provoke a cardiac tamponade.

This enhanced evacuation of blood from the pericardial cavity may result in reduced postoperative bleeding, which reduces the need of re-intervention for postoperative bleeding, blood transfusion and the risk of early or late cardiac tamponade. This clinical effect is illustrated in the example below representing a pilot study, wherein successful flushing of the pericardial cavity with an early prototype of a system without sensors but with manual control is described The flow rate control system is configured to control the ratio between the infusion liquid flow rate and the blood loss flow rate in the effusion liquid flow. By controlling a ratio between the infusion liquid flow rate and the blood loss flow rate in the effusion liquid flow, the amount of infusion liquid pumped to the pericardial cavity can be adapted to the amount of blood loss of the patient as calculated from the hematocrit sensor values. This ratio is important as the amount of infusion liquid pumped into the pericardial cavity is used to dilute the blood and clots in the pericardial cavity so that the blood can more easily be transported out of the pericardial cavity. When a relatively large amount of blood is present in the pericardial cavity and, as a result, in the effusion liquid also a relatively large volume of infusion liquid is desired to properly dilute the blood in the pericardial cavity without building up a too high pressure in the cavity which might provoke a cardiac tamponade. When the amount of blood in the effusion liquid is low a smaller volume of infusion liquid may be pumped to the pericardial cavity.

Preferably, the infusion liquid temperature is in a range of 36° C.-38° C., more preferably approximately 37° C.

The control unit is configured to determine the blood loss volume and/or blood loss volume rate from the pericardial cavity. On the basis of the information available in the control unit, the total volume of blood loss and/or the blood loss flow rate from the pericardial cavity can be determined. It is advantageous to monitor the total volume of blood loss and/or the blood loss flow rate, so that the condition of the patient can be monitored more accurately.

In an embodiment, the sensor signals comprise an infusion liquid signal representative for an infusion liquid volume pumped towards the pericardial cavity. In this embodiment, the volume of infusion liquid or flow rate of infusion liquid can be determined by a sensor. In an alternative embodiment, the flow rate of infusion liquid can be determined on the basis of the control signal used to control the pump device. Since the control signal is used to adjust the pump device to the desired flow rate of infusion liquid, the control signal can also be used to determine the infusion liquid flow rate, and the volume of infusion liquid pumped from the flushing system to the pericardial cavity.

The flushing system may comprise an infusion liquid flow sensor to determine the flow rate of the infusion liquid flow, wherein said determined flow rate of the infusion liquid flow is used as the infusion liquid signal. The flow rate may be determined by measuring the flow rate of infusion liquid by a flow rate sensor, but also by determining a change in volume or weight of an amount of infusion liquid in the flushing system. The flow rate may also determined by any other suitable sensor or device.

The system also comprises an effusion liquid flow sensor to determine a flow rate of the effusion liquid flow, and wherein the determined flow rate of the effusion liquid flow is used as the effusion liquid signal. The flow rate of the effusion liquid flow may be determined by any suitable sensor, for example a flow rate sensor arranged in an effusion liquid conduit running to a container for receiving effusion liquid. The flow rate of effusion liquid may also be determined by determining the increase in weight or volume of effusion liquid in one or more effusion liquid containers that receive effusion liquid flowed out of the pericardial cavity.

Importantly, the system also comprises a blood flow sensor to determine a value representative for the blood loss flow rate in the effusion liquid flow, and wherein the value representative for the blood loss flow rate in the effusion liquid flow is used as the blood volume signal.

According to the invention, the blood flow sensor is a hematocrit sensor configured to measure the hematocrit value of the effusion liquid flow. By measuring the hematocrit value of the effusion liquid flow the relative amount of blood in the effusion liquid flow can be measured. With this relative amount of blood in the effusion liquid in combination with the flow rate of effusion liquid, the blood loss flow rate in the effusion liquid flow can be calculated more accurately and provide a sensor signal to the control system for the infusion liquid flow.

Normally, the hematocrit sensor will meet one or more, preferably all, of the properties listed below;

1) The sensor should be able to measure accurately the hematocrit in a fluid that can pass an up to a 30 Fr (=10 mm) thoracic drain which is a preferred effusion drain as described below.

2) The measurements should be accurate until a hematocrit of 100% (clots)

3) The sensor should be capable of detecting clots and to quantify the amount of clots (per time unit)

4) The sensor should be able to cope with fast fluctuating levels of hematocrit at different flow rates of the effusion liquid 5) The sensor should be able to measure the hematocrit in an outflow drain that is completely filled, partially filled or empty (when air passes through)

6) The sensor should provide real time measurements

7) The sensor should be accurate at different temperatures in the range of 20-37° C.

8) The sensor should have at least two light sources at different wavelength

9) The technique should be safe.

10) The sensor should be capable of detecting air leakage at least semi-quantitatively.

11) The involved Software should be able to calculate the precise amount of blood loss per time unit from the hematocrit sensor signal and the outflow volume sensor signal, and should be able to do this real time Other sensors, such as inline spectral analysis sensors, may also be provided to determine relevant parameters of the effusion liquid flow, such as a relative blood volume and/or blood composition of blood in the effusion liquid flow.

Importantly, the system also comprises a pressure control system to control the pressure in the pericardial cavity, wherein the pressure control system comprises:

a pressure sensor to provide a pressure control signal representative for the pressure in the pericardial cavity a pressure control unit to adjust the infusion liquid flow rate to keep the pressure control signal within desired pressure limits so as to avoid acute cardiac tamponade.

The control unit is preferably integrated in the general control unit for the Infusion liquid flow Preferably, said pressure sensor is integrated in the wall of an integrated infusion and effusion drain as further explained below but may also be integrated into the infusion liquid tube or the effusion liquid tube in a position inside the pericardial cavity once the tubes have been inserted.

The pressure sensor is provided to determine the pressure in the pericardial cavity as exactly as possible. In the preferred embodiment where an integrated effusion drain is used as described below, the sensor is located at the proximal end or the drain which is located inside the pericardial cavity during use. The pressure sensor signal is used as an overriding signal to control the infusion liquid flow rate. When the pressure in the pericardial or thoracic cavity is low (for example <10 mm Hg, depending on the patient's clinical status) there is no limitation to increase the infusion liquid flow rate to the desired value. When the pressure in the pericardial cavity exceeds a certain value (for example >10 mm Hg, depending on the patient's clinical status) the infusion liquid flow rate can be limited or stopped to prevent cardiac tamponade.

In a preferred embodiment, the system also comprises a heater device configured to heat the infusion liquid to a desired infusion liquid temperature.

A suitable desired infusion liquid temperature is for example approximately 37° C., i.e. approximately equal to a normal body temperature of a person. The desired infusion liquid temperature may also be adapted or adjusted to the actual body temperature of the patient. This actual body temperature may be measured in any suitable way, and may for example be obtained of a general patient monitoring unit that measures body temperature of a patient.

In an alternative embodiment, a separate temperature sensor may be provided to determine an actual temperature of a patient. This temperature sensor may for example be arranged to measure the temperature within the pericardial cavity itself and may advantageously also be located at the proximal end of an integrated effusion drain as explained below.

In a further embodiment, the desired infusion liquid temperature may be selected to be higher or lower than the actual body temperature of the patient that is treated in order to warm up or cool down the patient, respectively. For example, when the body temperature of the patient to be treated is undesirably high, the desired infusion liquid temperature may be selected to be relatively low to cool down the patient. Correspondingly, when the body temperature of the patient to be treated is undesirably low, the desired infusion liquid temperature may be selected to be relatively high to warm up the patient.

In an embodiment, the system comprises a temperature control system to control a temperature of the infusion liquid flow, wherein the temperature control system comprises:

a temperature sensor to measure a temperature of infusion liquid, a temperature control unit to provide a temperature control signal on the basis of the measured temperature of infusion liquid and a desired infusion liquid temperature, and the heater device, wherein the heater device is actuable by the temperature control signal to heat the infusion liquid to the desired infusion liquid temperature.

By providing a temperature control system the temperature of the infusion liquid may be controlled more accurately.

Further, the system may comprise one or more effusion liquid containers to receive effusion liquid from the pericardial cavity. One or more effusion liquid containers may be arranged in the system to receive effusion liquid from the pericardial cavity. The one or more effusion liquid containers may be connected to an effusion liquid inlet of the flushing system configured to connect an effusion tube that provides a liquid connection between the body cavity and the effusion liquid inlet.

The flushing system may preferably comprise one or more suction devices to draw effusion liquid out of the pericardial cavity. The one or more suction devices may be arranged to create a relative low pressure in one or more effusion liquid containers to receive effusion liquid so that effusion liquid is drawn towards the one or more effusion liquid containers.

In an embodiment, the system comprises a display device, wherein the display device is configured to display relevant parameters, in particular infusion liquid flow rate, effusion liquid flow rate, blood loss flow rate, and trends thereof. A display device may also be used to display other relevant parameters of the flushing process. In particular, it may display warning signals provided by specific combinations of sensor signals as exemplified below.

The invention further provides a method of monitoring a blood loss volume or blood loss flow rate from (a body cavity, such as) the pericardium of a patient, comprising the steps further defined in claim 16

By determining, for example calculating, a blood loss volume or blood loss flow rate, the condition of the patient can be monitored more accurately, in particular during flushing of the pericardial cavity. The processing unit may for example be a control unit or another suitable processing device. The blood loss volume or blood loss flow rate is preferably registered in a storage device over the course of time so that the development of the blood loss volume or blood loss flow rate can also be monitored in the course of time.

In an embodiment, the method comprises the step of receiving in the control unit a signal indicating flow rate of effusion liquid from the pericardial cavity being provided from a sensor registering increased volume in a container (7) collecting effusion liquid.

In an embodiment, the method comprises the step heating or cooling the infusion liquid by a heater device, normally to a temperature in the range 36-38° C. and controlling the heater device either by the control unit controlling the pump for infusion liquid, by an independent control unit or manually by medical or non-medical staff.

In an embodiment, the method may further comprise the step of displaying, by a display device, the blood loss volume or blood loss flow rate from a body cavity.

In an embodiment, the method may further comprise the step of displaying instructions to involved medical or non medical staff monitoring the patient.

Further, the invention disclose a method of treatment of postoperative cardiac patients in order to reduce the risk of cardiac tamponade, reduce post-operative blood loss and reduce the accumulation of blood and clots in the pericardial cavity, wherein the pericardial cavity of the patient is flushed with a flushing system as defined in the present specification In the following is provided a more detailed explanation of different aspects of the invention and its clinical utility.

Unique Combination of Volume, Hematocrit and Pressure Sensing Resulting in Very Early Detection of Postoperative Bleeding and Threat of Acute Cardiac Tamponade After closure of the patients' chest, flushing therapy will start aiming for the dilution of whole blood (Ht 0.35-0.45) to at least 50% (Ht 0.17-0.23) in first instance. Flushing is continued until hematocrit levels drop below about 0.1 and blood loss (precisely calculated from volume and hematocrit sensor values) drops below about 10 ml/hour. The infusion liquid inflow will be gradually diminished and when Ht levels are below 0.05 during 3 hours, flushing therapy can be stopped.

Measuring the exact amount of blood loss during flushing therapy cannot be determined by calculating the in- and outflow volume difference alone for two reasons; 1) some (unknown) part of the infusion fluid may be left behind in the pericardial and/or thoracic space, and 2) during the first 24 hours after cardiac surgery the composition of the effusion liquid changes distinctly from whole blood (hematocrit 0.35-0.45) towards a more watery solution with low to very low hematocrit values approaching zero. Thus, the blood coming from the wound is not only diluted by the flushing system but also by the patients own wound effusion liquids.

Therefore, to determine the exact amount of blood loss according to the invention continuous measurement of the hematocrit value of the effusion liquid is undertaken. When knowing the total effusion liquid volume and the hematocrit value of this volume the exact amount of blood loss can be calculated or at least precisely estimated for any given time period. The patients' intravascular hematocrit value (normal range 0.35-0.45) can be used to determine a reference value. For example; when during 15 minutes an effusion liquid volume of 200 ml was measured with a mean hematocrit of 0.20, the volume needed to dilute patients' whole blood (for example hematocrit 0.40) to a hematocrit of 0.20 is 100 ml. Actual blood loss during this 15 minutes was 200-100=100 ml or, extrapolating 400 ml/hour.

In clinical practice, drain volume loss is observed per time unit, usually an hour, and on the basis of these data decisions are made. With the automated calculation of the exact amount of blood loss as described above, the amount of blood loss and especially the trend of blood loss can be determined over much smaller time frames, for example every 5 minutes. In this way, trends towards an increase, consistent or decrease of blood loss can be determined more precisely and more importantly, faster. Increased and/or excessive blood loss will be detected earlier, resulting in more time to organize reoperation thereby decreasing the risk of hypovolemia and/or acute cardiac tamponade resulting in circulatory collapse of the patient. Thus, the earlier detection made possible by the invention will contribute to patients' safety.

Acute cardiac tamponade can develop rapidly with a range of 15 minutes to several hours. The complete circulatory collapse of the patient is always preceded by a period (minutes to hours) of increased intrapericardial pressure in combination with an increase in blood loss or sudden decrease in outflow liquid volume (indicating outflow drain obstruction). The exact blood loss values in combination with the intrapericardial pressure sensor values are used for very early detection of increased threat of cardiac tamponade. Short (several seconds) changes in values of hematocrit, volume and pressure sensors may be due to awakening/movement or coughing of a patient. The flushing device according to the invention will be able to give a gradual alarm and treatment advice shown in a display when a combination of changes are consistent during several minutes, for example at least five minutes. Thus, when during a 5-minute period the following situations occur:

1) There is a trend towards an increase in blood loss (precisely calculated from volume and hematocrit sensor values) in combination with an increase in intrapericardial pressure there is a highly increased risk of surgical bleeding and acute cardiac tamponade. The warning/advice on the device display might be: "acute threat of cardiac tamponade, strongly consider emergency reoperation". The sensor signals can cause the device to stop flushing.

2) There is a trend of increasing intrapericardial pressures in combination with a sudden decrease in outflow liquid volume (possibly indicating drain obstruction), the warning/advice might be: "acute threat of acute cardiac tamponade, possible drain obstruction, strongly consider emergency reoperation". The sensor signals can cause the device to stop flushing.

3) There is an increase in blood loss but intrapericardial pressures remain unchanged or lower, the warning/advice on the device display might be: "increased blood loss, carefully monitor all values (volume, hematocrit and pressure) during the next time period. The sensor signals can cause the device to increase the inflow liquid volume.

4) There is a consistent amount of blood loss during the first hours after cardiac surgery but no trend to decrease (according to values of table 5-6), the alarm/advice might be: "increased risk of postoperative bleeding requiring reoperation, carefully monitor all values (volume, hematocrit and pressure) during the next time period".

5) There is a constant inflow of infusion liquid and hematocrit levels rise, the alarm/advice might be: "increased blood loss requiring reoperation, carefully monitor all values (volume, hematocrit and pressure) during the next time period". The sensor signals can cause the device to increase the inflow liquid infusion in order to lower viscosity, enhance evacuation of blood and decrease the bleeding tendency.

6) The intrapericardial pressures exceed an upper limit threshold depending on patients condition; for patients on mechanical ventilation 12-15 mmHg and patients with normal breathing 8-12 mmHg, the alarm/advice might be: "increased risk of acute cardiac tamponade, possible drain obstruction, consider reoperation". The signals can cause the device to stop the inflow liquid infusion.

7) Outflow infusion liquid volume is >200 ml less than infusion liquid volume and constant intrapericardial pressure, the alarm/advice might be: "Danger of fluid accumulation in pleural and/or pericardial cavity, possible drain obstruction, consider X ray photography of pleural spaces and/or echocardiographic examination of the pericardial space". However, not every negative fluid balance will lead to termination of flushing therapy as long as there is no increase in pressure in the pericardial cavity. If negative fluid balance persists and reaches an upper threshold (for instance 500 ml) flushing therapy can be (temporarily) stopped. Automatic milking (see below) can start to resolve a possible drain obstruction (see below).

8) There is a decrease in blood loss (precisely calculated from volume and hematocrit sensor values), total amounts not exceeding values of table 5-6, and a constant intrapericardial pressure below the upper limit or decreasing pressure; the advice can be: "flushing therapy adequate, continue flushing therapy".

In this way the flushing device according to the invention will not only secure its own safe functioning but it will also be much safer than any nurse or doctor dependent "clinical observational" systems by A) detecting and quantifying a postoperative bleeding faster and more accurately and B) by detecting (the threat) of acute cardiac tamponade much faster.

Early Detection of Drain Occlusion and "Automatic Milking" To Resolve Drain Occusion In addition to the alarm and safety measures above an additional mechanism may be added to treat drain occlusion when flushing therapy alone was not sufficient and obstructing clots developed despite the flushing therapy, resulting in drain clogging.

In common clinical practice as well as in flushing systems according to the invention, the outflow through the outflow wound drains is enhanced by applying continuous negative pressure suction of e.g. 20 cm of water pressure. When it is the doctors' or nurse' impression that drains are partially or completely blocked, they will start to "milk" the outflow drains by manually applying rapidly alternating slightly positive or zero pressure and higher negative pressures by pressing and releasing the drains alternately with two hands. In this way the clots obstructing the drains can often be mobilized and normal drain function restored.

When drain obstruction occurs, negative pressure in the outflow drain will be constantly applied negative pressure of e.g. 20 cm of water pressure and situation 2, 6 or 7 (see above) will occur, indicating a high chance of drain obstruction. In this situation, an embodiment of the flushing system according to the invention will immediately apply "automatic milking" to the outflow drains by mechanical means (pressing and releasing of a segment of the outflow drain by an electromotor or electromagnet mechanism) or electronic means (by controlling a negative pressure suction pump), to resolve drain occlusion. This can be repeated until outflow drain function is restored and situations 2, 6 or 7 are discontinued.

When a high amount or an increase in clots is detected, in combination with a trend towards decreased outflow, automatic milking will start to prevent drain obstruction by clots.

BRIEF DESCRIPTION OF THE DRAWINGS

An embodiment of a flushing system according to the invention will now be described in further detail, by way of example only, with reference to the accompanying drawings, in which:

FIG. 3a illustrates a cut-through view of the drain tube at the position of a liquid outlet; FIG. 3b illustrates a cut-through view of the drain tube at a position with no liquid outlet.

DETAILED DESCRIPTION

Figure 1:
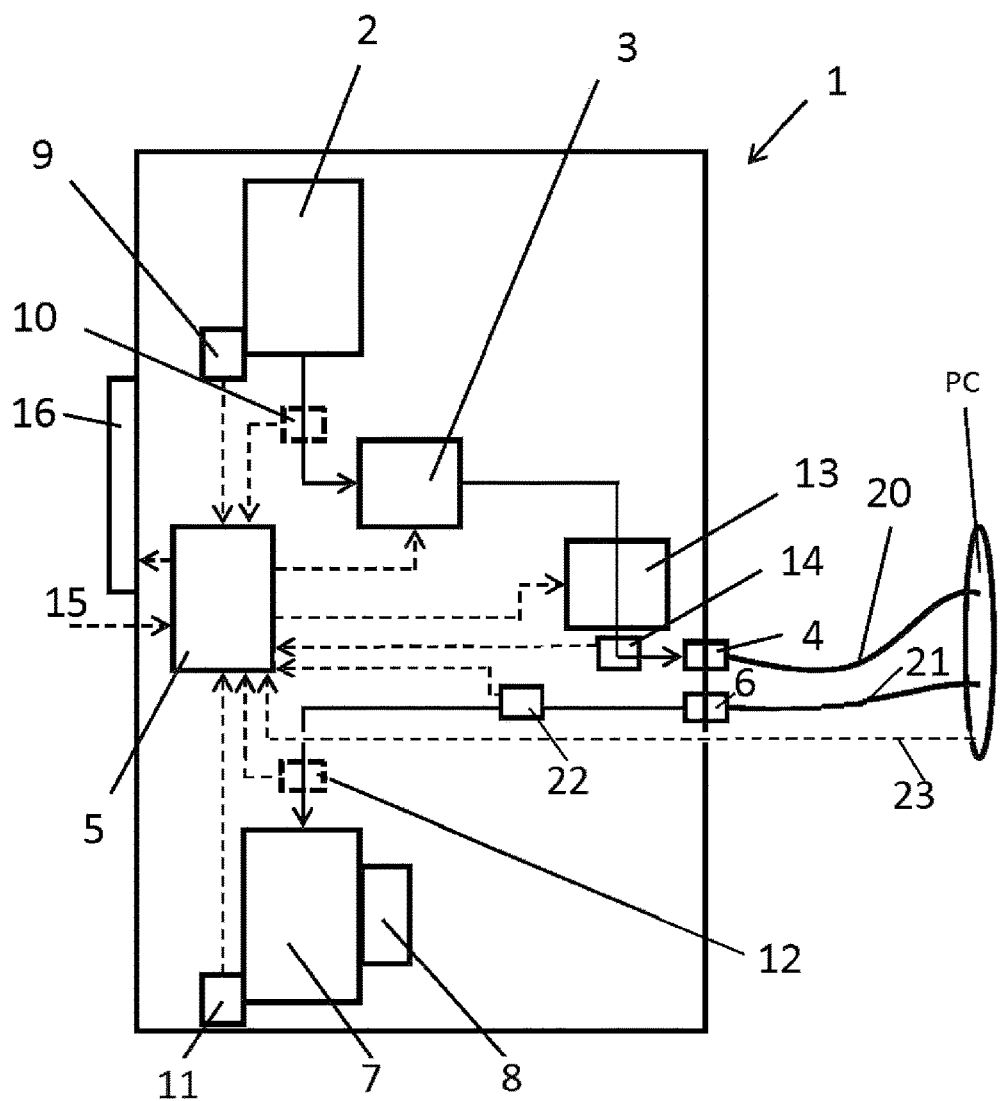
FIG. 1 shows schematically a pericardial flushing system according to the invention.

FIG. 1 shows schematically a pericardial flushing system, generally denoted by reference numeral 1. The flushing system 1 is configured for continuous flushing of the pericardial cavity, in particularly as a post-operative treatment. During continuous flushing of the pericardial cavity infusion liquid is pumped into the cavity to dilute blood and clots present in the cavity. At the same time effusion liquid, i.e. a mixture of blood and infusion liquid mixed in the pericardial cavity is drawn out of the cavity in order to remove the blood and clots from the cavity.

The flushing of the pericardial cavity is preferably started directly after operative treatment and is for example continued for 12-24 hours.

Such continuous flushing may for example be used to flush a pericardium of a patient after cardiac surgery, and may have a reducing effect on postoperative bleeding.

The flushing system 1 comprises one or more containers 2 containing infusion liquid, for example a number of bags containing saline fluid, such as NaCl 0.9%, as known in the art. The one or more containers 2 are connected to a volumetric pump device 3 configured to pump infusion liquid with a desired flow rate towards an infusion liquid outlet 4. The pump device 3 may be any suitable pump device for infusion liquid, and is preferably of a type that allows pumping at a relative accurate flow rate. The volumetric pump device 3 may for example comprise inlet and outlet ports, a pump element and a drive element for driving the pump element to pump infusion liquid at a desired flow rate.

The infusion liquid outlet 4 is configured to connect a first tube 20 having an infusion liquid lumen to guide the infusion liquid flow from the flushing system 1 to the pericardial cavity PC of a patient to be treated.

The infusion liquid flow rate of the pump device 3 is adjustable by a control unit 5 so that the control unit 5 can control the flow rate of infusion liquid that is pumped to the pericardial cavity PC based on signals from multiple sensors as described elsewhere The flushing system 1 further comprises an effusion liquid inlet 6 to connect a second tube 21 having an effusion liquid lumen to guide effusion liquid from the pericardial cavity PC of the patient to be treated to the effusion liquid inlet 6. It is remarked that, generally, the first tube 20 and the second tube 21 in a preferred embodiment are combined together with further functionalities in a multi lumen tube device in the form of an integrated drain device as described elsewhere.

In the flushing system 1, the effusion liquid is guided to one or more effusion liquid containers 7 arranged in the flushing system 1. Next to the effusion liquid containers 7, one or more suction devices 8 are arranged. The suction devices 8 are configured to create a relative low pressure, i.e. an underpressure of for example—15 mmHg, in the one or more effusion liquid containers 7. This relative low pressure is used to draw effusion liquid from the pericardial cavity PC towards a respective effusion liquid container 7.

A weight sensor 9 is provided to measure a change in weight of the infusion liquid in the one or more infusion liquid containers 2. This change in weight is representative for a decrease in the volume of infusion liquid in the one or more infusion liquid containers 2. On the basis of the change of volume of infusion liquid over the course of time, the flow rate of infusion liquid towards the pericardial cavity PC may be determined.

The weight sensor 9 or the control unit 5 may be configured to determine the flow rate of infusion liquid pumped out of the one or more infusion liquid containers. It is remarked that any other sensor configured to determine the flow rate of infusion liquid towards the pericardial cavity PC may be used. For example, the flow rate of infusion liquid may be determined by a flow rate sensor 10 which may be located anywhere in the infusion part of the system. It is remarked that the flow rate of infusion liquid may also be deducted from a control signal provided by the control unit 5 to adjust the flow rate of volumetric pump device 3 in response to one or more of the sensor signals described below. Any other way to determine the flow rate of infusion liquid may also be used.

Effusion liquid that flows out of the pericardial cavity PC due to the suction provided by the one or more suction devices 8 is received in the one or more effusion liquid containers 7 resulting in an increase of volume of effusion liquid in these effusion liquid containers 7. This increase of volume in the one or more effusion liquid containers 7 may be determined with a weight sensor 11 configured to determine a volume/weight of effusion liquid in the one or more effusion liquid containers 7. On the basis of the change of volume/weight of effusion liquid over the course of time, the flow rate/volume of effusion liquid may be determined.

Any other sensor configured to determine the flow rate of effusion liquid from the body cavity PC to the one or more effusion liquid containers 2 may also be used to calculate the flow rate/volume of effusion liquid. For example, the flow rate of effusion liquid may be determined by a flow rate sensor 22.

The sensors 9, 11, the control unit 5 and the pump device 3 form a flow rate control system to control a flow rate of the infusion liquid flow at the infusion liquid outlet 4 on the basis of the sensor signals, the sensor signals comprising an infusion liquid signal representative for an infusion liquid flow rate towards the pericardial cavity PC and an effusion liquid signal representative for an effusion liquid flow rate from the pericardial cavity PC. Generally, the difference between the infusion liquid flow rate and the effusion liquid flow rate corresponds substantially to the blood loss flow rate of the patient from the pericardial cavity PC. Importantly, the control signals also comprise a hematocrit sensor signal and a pressure control signal as explained below.

On the basis of the calculated blood loss volume and/or flow rate, a suitable infusion liquid flow rate can be pumped by the pump device 3. It has been found that an infusion liquid flow rate of at least once preferably at least one and a half or twice the blood loss flow rate, with an infusion liquid temperature of approximately 37° C., provides sufficient infusion liquid to properly dilute blood and cloths in the pericardial cavity PC. This results in a more fluid substance with lower viscosity in the pericardial cavity PC which will pass more easily through the tube 21 without obstructing it.

Since it is important to accurately determine the actual blood loss volume from the pericardial cavity PC a hematocrit sensor 12 is provided to generate a blood flow signal representative for the relative amount of blood or composition of the blood in the effusion liquid. The actual blood loss will be calculated from the outflow volume and the hematocrit sensor values of the blood flow. Alternatively, is provided a sensor that performs a continuous spectral analysis of the effusion liquid to determine relative blood content or blood composition in the effusion liquid flow. In the present context a "hematocrit sensor" is intended to cover both alternatives iThis blood flow sensor signal is also provided as an input to the control unit 5 in order to control the infusion flow rate of infusion liquid pumped towards the pericardial cavity PC.

Importantly, the system also comprises a pressure control system to control the pressure in the pericardial cavity. The pressure control system comprises a pressure sensor 23 to provide a pressure control signal representative for the pressure in the pericardial cavity. The sensor is connected to a pressure control unit to adjust the infusion liquid flow rate to keep the pressure control signal within desired pressure limits so as to avoid acute cardiac tamponade. The pressure control unit is preferably integrated in the general control unit for the Infusion liquid flow. Preferably the pressure sensor is integrated in an integrated outflow drain device as explained in connection with FIGS. 2 and 3, but might alternatively be located on the distal part of first or second tube 20 or 21 which is positioned in the pericardial cavity when in use.

The flushing system 1 comprises a heater device 13 to the heat infusion liquid that is pumped to the pericardial cavity PC to a desired infusion liquid temperature. This desired infusion liquid temperature may for example be in the range 36° C.-38° C., for example approximately 37° C. The heater device 13 may be any device suitable to heat up the infusion liquid to this desired temperature, but is preferably an instantaneous heater which is capable to heat up the infusion liquid to the desired temperature while it continuously flows through the heater device 13. The heater device 13 may comprise a thermostat or other suitable device to heat the infusion liquid to the desired temperature.

In a further embodiment, the system 1 may comprise a temperature control system comprising a temperature sensor 14 to measure a temperature of infusion liquid, the control unit 5 to provide a temperature control signal on the basis of the measured temperature of infusion liquid and a desired infusion liquid temperature, and the heater device 13 that is actuable by the temperature control signal to heat the infusion liquid to the desired infusion liquid temperature.

Such temperature control system may increase the accuracy of the infusion liquid temperature, and may provide more flexibility in adapting the desired infusion liquid temperature. It is remarked that the control of the temperature control system does not have to be integrated in the control unit 5, but may also be formed by a separate control unit, for example a part of the heater device 13, or may be integrated in another control device or processing unit.

The desired infusion liquid temperature may be adapted or adjusted to the actual body temperature of the patient. This actual body temperature may be measured in any suitable way, and may for example be obtained from a general patient monitoring unit that measures body temperature of a patient. This actual body temperature may be fed to the control unit 5 as an input signal 15.

The desired infusion liquid temperature may be selected to be at the same level as the actual body temperature of the patient, but also at a higher or lower level than the actual body temperature of the patient that is treated. Such higher or lower infusion liquid temperature may be used to warm up or cool down the patient, respectively.

For example, when the body temperature of the patient to be treated is undesirably high, the desired infusion liquid temperature may be selected to be relatively low to cool down the patient. Correspondingly, when the body temperature of the patient to be treated is undesirably low, the desired infusion liquid temperature may be selected to be relatively high to warm up the patient. Preferably, a temperature sensor is also integrated in an outflow drain device as explained below in connection with FIGS. 2 and 3.

Since the control unit 5 may determine a blood loss volume or blood loss flow rate from the pericardial cavity PC of a patient based on input from the hematocrit sensor this determined, in particular calculated, blood loss volume or blood loss flow rate may also be used to monitor the blood loss from the pericardial cavity PC.

For example, the determined blood loss volume or blood loss flow rate may be displayed by a display device 16 so that a physician or nurse can easily monitor the development of the blood loss over time. Such display device 16 may also be used to display any other relevant parameter of the flushing process, such as used volume of infusion liquid, volume of received effusion liquid, flow rates of infusion liquid and effusion liquid, relative blood content in effusion liquid, composition of blood in effusion liquid, and trends thereof. Importantly, the display may show instructions based on the combined sensor input as explained elsewhere The blood loss volume, blood loss flow rate or other relevant parameters may also automatically be monitored by an alarm device, for example integrated in control unit 5, that issues an alarm signal when the blood loss volume and/or blood loss flow rate and/or other parameters exceeds a threshold value. The alarm signal may be any suitable signal such as a visible or an audible signal.

It is remarked that instead of control unit 5, any other (processing) unit or device may also be used to determine/calculate the blood loss volume or blood loss flow rate based on input from the hematocrit sensor.

Figure 2:
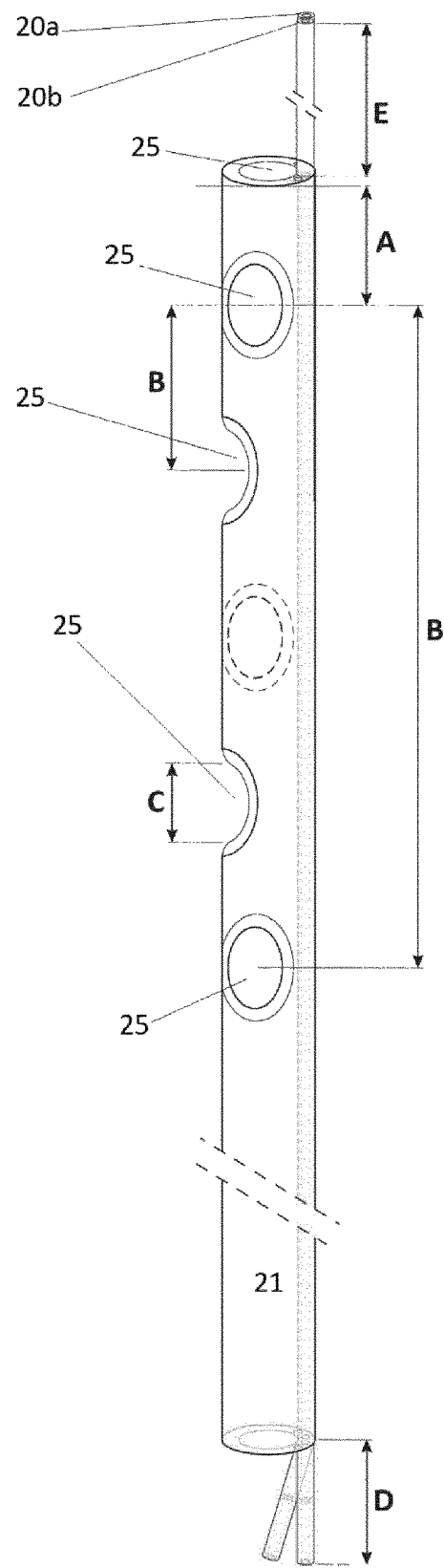
FIG. 2 shows schematically a preferred embodiment of the flushing system where different functionalities are integrated in an outflow drain device.
Figure 3A:
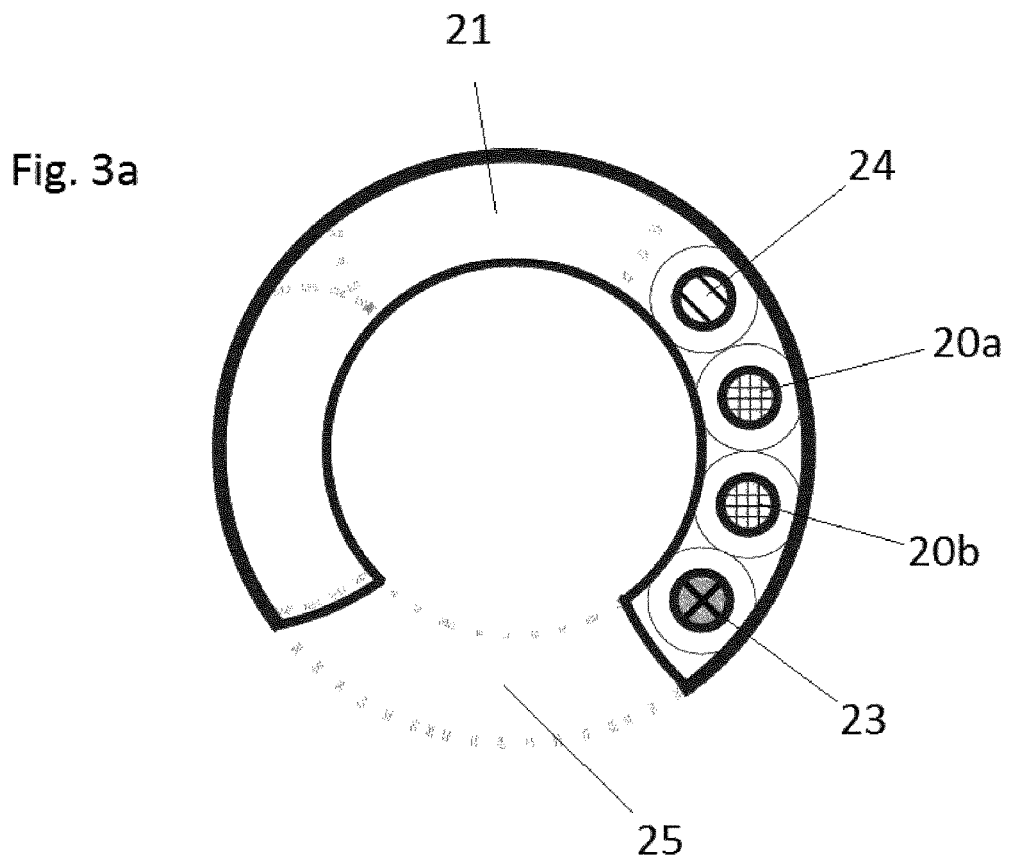
FIGS. 3a and 3b shows a cut-through view of the preferred embodiment of the outflow drain device.
Figure 3B:
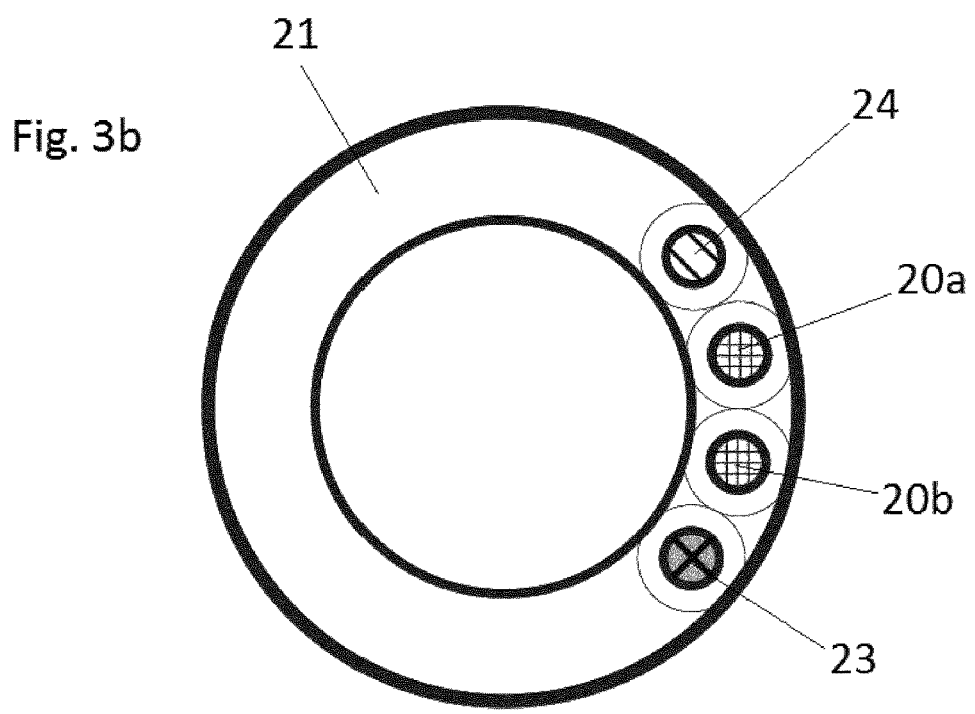

FIGS. 2 and 3 illustrate how different functionalities and tubes might be integrated in one drain device. FIG. 2 shows a second tube 21 used for draining liquid from the pericardial cavity (PC). The tube 21 is provided with a multiplicity of relatively large openings 25 providing outlets for the liquid in the pericardial cavity from different positions. The embodiment of FIG. 2 is provided with 6 outlet openings, generally the number of outlets depends on length of the tube 21 positioned in the pericardial cavity and the diamenter of the tube. The outlets of the side of the walls of the embodiment shown in FIG. 2 are round having a diameter C which diameter depend of the diameter of the tube 21 but which is normally in the range 5-10 mm. The distance B defines the distance between the centers of two neighbouring outlets, which is normally in the range normally between 15-25 mm. In the shown embodiment of FIG. 2 A is 13 mm, B is 19.5 mm, C is 7.7 mm, D is 50 mm and E is 300 mm.

1) An inflow liquid tube is advantageously integrated in the outflow liquid tube 21 in such a way that the infusion liquid tube does not consume lumen of the outflow tube. In the embodiment of FIG. 2-3, two infusion liquid tubes 20*a*, 20*b* are positioned in the wall of the outflow tube. However, the inflow liquid tube(s) 20 might also be positioned in a parallel position outside the wall of the outflow liquid tube 21.
2) Generally, an outlet though which at least a part of the inflow liquid leaves the inflow liquid canal is preferably positioned at some distance of the inlet of the outflow tube to prevent the inflow liquid from leaving the pericardial cavity immediately by the shortest pathway out of the pericardial cavity through the outflow tube and thereby not flushing the pericardial cavity. In the embodiment of FIG. 2 this distance is indicated with E. Normally, 200 mm<E<400 mm, and in the shown embodiment, E=300 mm. The inflow liquid tube(s) can be easily tailored to a desired length.
3) Generally, it is advantageous to have at least two inflow canals connected to each outflow tube in order to reach more areas in the pericardial cavity.
4) The pressure sensor can advantageously also be integrated in the one drain device in order to measure an exact pressure at the proximal end of the outflow liquid tube 21 in a central position in the pericardial cavity. A possible position is illustrated in FIG. 3 where the pressure sensor is placed in the wall of the outflow liquid tube 21. As for the position of the inflow liquid tube(s) it is important that the pressure sensor 23 does not disturb the flow through the outflow liquid tube 21. In common clinical practice only the central venous pressure is used as a derivative measure for the pericardial pressure. However, the central venous pressure is often not reliable and not measured constantly and accurately.
5) A temperature sensor 24 can preferably also be integrated in the outflow liquid tube 21 in order to provide an exact measure of the central body temperature. The signal from such a temperature sensor can provide or replace a signal 15 from an external source. A possible position is illustrated in FIG. 3 where the temperature sensor is placed in the wall of the outflow liquid tube 21. As for the position of the inflow liquid tube(s) and the pressure sensor, it is important that the temperature sensor 24 does not disturb the flow through the outflow liquid tube 21. In common clinical practice the rectal or pharyngeal temperature is used to estimate the patients temperature but these are not accurate and often disturbed and interrupted measurements.

Integration of these functionalities in one outflow drain device is highly preferred for accurate measurements and because:
1) All sensors and inflow liquid canals are inserted through the same opening in the skin and therefore there is no need for extra skin incisions leading to a higher infection rate and worse cosmetic outcome.
2) Separate inflow canals and sensor canals through one incision will lead to leakage of fluid alongside the outflow drain because mutual round structures will never perfectly fit in one round skin opening.
3) The system will be easy to use while insertion of the different functionalities will cost no extra time for the surgeon.

The design of the outflow drain device can be based on the standard pericardial/thoracic drain used in cardiac surgery. An example of a standard drain is a 60 Shore A Silicon drain implantable for up to 30 days. The OD (outer diameter)=11.0 mm (=33 FR.) ID (inner diameter)=7.0 mm.

Advanced Design of the Pericardial Flushing System

In an advanced design the blood loss measurements of the flushing device according to the invention can be combined with other signals like the continuous measurement of patient's actual body weight and/or the total of infused fluid volume intravenously into the patient. Also hemodynamic and intravascular measurements can be included. Knowing baseline hemoglobin and hematocrit levels of the patient, it will allow making a precise prognosis of the expected patients extravascular fluid balance and intravascular hemoglobin and hematocrit levels. This can result in a well founded choice whether or not to give blood transfusion, i.e. a transfusion advice. The clinical impact of this decision-making process is explained above.

In Summary

The Pericardial Flushing System according to the invention will enhance the evacuation of blood and clots from the pericardial cavity by flushing the cavity with saline (or other low viscosity solution). By the unique combination of continuous intrapericardial pressure sensing, continuous hematocrit sensing of outflow liquids and continuous sensing of in and outflow volumes, increased postoperative bleeding requiring reoperation can be determined much faster and more accurately then by clinical observation. At the same time the system will be able to detect the emergence of a life threatening acute cardiac tamponade requiring urgent reoperation much faster than by clinical observation and before hemodynamic deterioration occurs. In addition a mechanism of automatic drain milking may be added to enhance the passage of clots through the outflow drain, diminish the chance of permanent drain obstruction and to resolve drain obstruction immediately after detection.

Moreover, in comparison with common clinical practice, the system will deliver some extra and more accurate measurements of important clinical parameters like intrapericardial pressure an central body temperature. By hematocrit analysis of the outflow fluids, the exact amount of blood loss can be calculated more accurately. This will improve clinical decision making with regard to optimal timing of re-exploration and blood transfusion policy.

The flushing and cleaning of the pericardial space will also reduce blood loss by preventing blood and clots from accumulating in the pericardial space. Blood and clots induce high fibrinolytic activity and will promote more bleeding.

Blood and clots that remain after chest tube removal can induce several postoperative complications related to the inflammatory reaction caused by the blood remnants for example, rhythm disturbances and pericardial adhesion formation. Leaving a clean pericardial space will reduce these complications. The blood cells that remain in the pericardial cavity will be subject to lysis of cell membranes leading to high concentration of free hemoglobin levels. These macromolecular proteins will lead to a high osmotic pressure and attraction of more fluid. This will lead to sometimes lethal late cardiac tamponade.

An integrated outflow drain device will provide an efficient and safe use of the system.

Example (Pilot Study)

Abstract

OBJECTIVES: To evaluate safety and feasibility of postoperative pericardial flush (PPF) after cardiac surgery.

METHODS: Postoperative pericardial flush was performed in 21 patients with CHD between November 2011 and April 2012 and results were compared to a retrospective CHD control group (n=127). From sternal closure up to 12 hours postoperatively, an infusion liquid (NaCl 0.9%; 40° C.) was delivered to the pericardial cavity using a volume controlled flushing system connected to an inflow Redon drain, which was inserted through one of the chest tube incision holes. Mean age was 44.5 (range 21.1-68.2) years and 10 (52.4%) were male. Redo surgery for congenital heart disease was performed in 10 (47.6%) patients of which pulmonary valve replacement in 8 (38.1%); mitral valve repair in 1 (4.8%) and atrial baffle replacement in 1 (4.8%). Right-sided intracardiac surgery was performed in 10 (47.6%) and left-sided intracardiac surgery in 7 (33.3%).

RESULTS: Postoperative pericardial flush was successfully completed in 20 (95.2%) patients. In 1 (4.8%) patient, PPF was stopped 3.5 hours postoperatively due to accumulation of >400 ml fluid in the right pleural cavity. There were no system related complications or infections. One patient needed pericardial drainage for late tamponade, likely to be related to anti-coagulant therapy. Patients receiving PPF showed a significant decrease in postoperative blood loss 12 hours postoperatively (mean difference=−213 ml, 95% CI: −37 ml to −389 ml; p=0.018) was small/moderate (eta squared=0.038).

CONCLUSIONS: Our findings support technical feasibility and safety of postoperative pericardial flush in patients undergoing cardiac surgery. Future studies to evaluate both short and long-term effects are needed.

Introduction

The general accepted amount of postoperative blood loss after cardiac surgery, varies greatly between 300 and 1500 ml during the first 12 hours postoperatively and is evacuated from the pericardial (and/or pleural) cavity using chest tubes. However, when blood loss within this timeframe is excessive or when cloths start to develop more rapidly, the drains often fail in their function to evacuate al blood, resulting in stasis of cloths and blood in the pericardial (and/or pleural) cavity. As a consequence this leads to high fibrinolytic activity, maintenance of blood loss and in some cases reoperation for bleeding and/or early cardiac tamponade. A surgical cause for bleeding is only found in half of patients undergoing reoperation/re-exploration for bleeding and in the remainder of patients the cause is multifactorial and probably an acquired/surgical related haemostatic defect is responsible for diffuse mediastinal haemorrhage. Intraoperative removal of the remaining blood and cloths, by means of flushing the pericardial cavity with warm saline, is often enough to stop the bleeding. It was this remarkable phenomenon that has lead to the hypothesis that postoperative blood loss and stasis of blood in the pericardial space could be a common determining factor for several postoperative complications. A continuous postoperative pericardial flushing system could promote the evacuation of activated and contaminated blood and cloths out of the pericardial cavity of patients that need cardiac surgery; hereby potentially controlling and stopping postoperative bleeding in an early stage and leaving a cleaner pericardial space behind after chest tube removal. When proven safe, feasible and clinically relevant a new therapeutic solution could be introduced that could be used in all patients that need cardiac surgery and on a global scale. The main focus of this pilot study is to evaluate the safety and feasibility of this pericardial flushing system after cardiac surgery. Secondary objectives include evaluation of chest drain production at ICU arrival, 6 and 12 hours postoperative. To our knowledge, this is the first study on the effectiveness of continuous postoperative pericardial flush therapy in cardiac surgery.

Abbreviations and Acronyms:
ALCAPA=Anomalous Left Coronary Artery from the Pulmonary Artery
AMC=Academic Medical Center, Amsterdam, The Netherlands
CHD=Congenital Heart Disease
CPB=Cardio-Pulmonary Bypass
ICU=Intensive Care Unit
PPF=Postoperative Pericardial Flush
TF=Tissue Factor
TGA=Transportation of the Great Arteries
t-PA=tissue Plasminogen Activator
TTE=Transthoracic Echocardiogram Patients and Methods Study Design and Patients Postoperative Pericardial Flush (PPF) was performed in a total number of 21 patients with congenital heart disease at the Academic Medical Center Amsterdam (AMC) from November 2011 to April 2012. All patients undergoing surgical correction for CHD were eligible to participate in this study. Patients were excluded in case of: emergency surgery, a history of bleeding diathesis or coagulopathy, participation in any study involving an investigational drug or device or when the patients had the inability to understand the study information and/or sign informed consent. Surgery was performed by a single surgeon in a single centre. Chest drain production at ICU-arrival, 6 and 12 hours postoperatively were compared to a retrospective control group consisting of a 127 CHD patients that underwent cardiac surgery, performed by the same surgeon, between January 2010 and December 2011. Median age at time of operation was 44.5 (range 21.1-68.2) years and 11 (52.4%) were male. Primary cardiac surgery was performed in 11 (52.4%) patients of which Redo surgery for CHD was needed in 10 (47.6%) patients of which pulmonary homograft placement in 6 (75.0%) patients, atrial baffle replacement in 1 (12.5%) patient and mitral valve repair in 1 (12.5%) patient.

Diagnosis among the 10 patients that needed primary correction for CHD were: ALCAPA in 2 (9.5%), Scimitar syndrome in 1 (4.8%) and PAPVD in 1 (4.8%). Preoperative left ventricular ejection fraction (LVEF) was >50% in 16 (76.2%), 30-50% in 5 (23.8%) and <30% in none.

Postoperative Pericardial Flush (PPF)

PPF aims to reduce postoperative blood loss by means of removing contaminated pericardial blood and clots via dilution and a continuous circulation of infusion liquid through the pericardial cavity. The PPF system is designed to flush a body cavity, in particular thoracic pleural and/or pericardial cavity, of a patient and it comprises: an infusion liquid solution (NaCl 0.9% 2 L bags) connected to a standard infusion liquid tube that runs through and connects a pump device (Braun Infusomat® Space) with a fluid heating device (Enflow® fluid warmer) and which is continuous with an infusion liquid tube that was inserted into the pericardial cavity thorough the same incision as one of the chest tube incision holes. The outflow tract was a closed low-vacuum (15 $cmH_2O$) collection system comprising standard chest tubes that evacuated outflow liquid from each opened body cavity (pericardial and/or pleural) separately into standard postoperative blood collection containers. Pericardial flush was performed continuously after operation, starting at sternal closure until approximately 12 hours postoperative. The infusion liquid flow rate was a constant 500ml/hour during the first two hours, after which the infusion liquid flow rate was volume controlled so that the infusion liquid volume was adjusted to a 1:1 ratio with patients' blood loss; with a minimum infusion liquid flow rate of 100 ml/hour. The infusion liquid (NaCl 0.9%) was delivered to the patient at a constant temperature of 40° C. to avoid changes in patient core temperature. The system in-and output was monitored every 15 minutes in the first two hours postoperatively and hourly thereafter. In addition to standard protocol, a secondary fluid balance was kept to calculate and monitor patients' actual blood loss and trace possible fluid accommodation. Fluid replacement and/or blood transfusion were given according to standard ICU protocol.

Follow-Up

Transthoracic echocardiograms (TTE) were the primary imaging modality to evaluate whether patients had pericardial effusion immediate postoperatively and at discharge. All patients had a TEE before discharge from hospital. Chest radiography was the primary imaging modality to evaluate pleural effusions. All patients had chest radiographs immediately at ICU arrival, 5-7 days postoperative and at discharge. Patients were followed by the referring cardiologists in our adult congenital heart clinic and were contacted for echocardiographic analysis six months postoperatively.

Statistical Analysis

Continuous variables are shown as mean with standard deviation unless otherwise noted. Categorical variables are shown as a percentage. In all cases a p-value of less than 0.05 was considered statistically significant. All data analyses were performed using with SPSS 20.0 for Windows (IBM® SPSS® Software).

RESULTS

Operative Data

Redo surgery for congenital heart disease was needed in 10 (47.6%) patients of which pulmonary valve replacement in 8 (38.1%); mitral valve repair in 1 (4.8%) and atrial baffle replacement in 1 (4.8%). Primary correction for CHD was needed in 4 (19.1%) patients: 2 (9.5%) for ALCAPA, 1 (4.8%) for Scimitar syndrome and 1 (4.8%) for PAPVD. Other procedures involved pulmonary homograft and LPA stent in 1 (4.8%), David procedure in 1 (4.8%) and Re-Bentall procedure in 1 (4.8%). An atrial septal defect (ASD) was closed in 4 (19.1%) and a ventricular septal defect was closed in 2 (9.5%) patients. Atrioventricular valve repair was performed in 11 (52.4%) of which mitral valve repair in 4 (19.1%), tricuspid valve repair in 6 (28.6%) and tricuspid replacement in 1 (4.8%). Overall, right-sided intracardiac surgery was performed in 10 (47.6%) and left-sided intracardiac surgery in 7 (33.3%). Feasibility Continuous postoperative pericardial flush was successfully completed in 20 (95.2%) patients. In 1 (4.8%) patient, PPF was stopped 3.5 hours postoperatively due to accumulation of >400 ml fluid in the right pleural cavity. There were no system related complications.

Postoperative Blood Loss

An independent-samples t-test was conducted to compare postoperative blood loss for the PPF-and the control-group. There was no significant difference in postoperative blood loss at ICU arrival (PPF-group: mean=99 ml, SD=190; control-group: mean=147 ml, SD=127; t (145)=−1.453, p=0.148) and 6 hours postoperatively (PPF-group: mean=284 ml, SD=215; control-group: mean=405 ml, SD=304; t (145)=−1.714, p=0.089). However, there was a significant difference in blood loss at 12 hours postoperative (PPF-group: mean=329 ml, SD=304; control-group: mean=543 ml, SD=379; t (145)=−2.402, p=0.018). The magnitude of the significant difference in means (mean difference=−213 ml, 95% CI: −37 ml to −389 ml) was small/moderate (eta squared=0.038).

Postoperative Complications

At discharge chest radiograph showed a trace/mild pleural effusion in 11 patients of whom a pleural cavity was opened in 5; transthoracic echocardiography showed pericardial effusion in 8 patients, of which 6 (75%) had <50% local pericardial effusion and 2 (25%) had >50%, >6 mm, circular pericardial effusion. One patient needed pericardial drainage for late tamponade, likely to be related to anti-coagulant therapy.

Comment

Blood Loss

The most important complication of cardiac surgery is (excessive) postoperative bleeding, resulting in increased chest tube production (>2 L/24 hours or >200 mL/hour) and is associated with higher mortality through mechanisms not related to blood transfusion. Predictive factors for hemorrhage and reoperation/re-exploration following cardiac surgery include: age, obesity, renal insufficiency, cardiopulmonary bypass (CPB) time and intracardiac repair. Reoperation/re-exploration for bleeding is a strong independent risk factor for adverse outcomes following cardiac surgery.

Specifically, operative mortality, prolonged mechanical ventilation, acute respiratory distress syndrome, sepsis, and atrial arrhythmias are increased in these patients. In addition, postoperative bleeding requiring multiple transfusions and surgical re-exploration is associated increased sternal wound infection, transfusion-related infection and higher costs. The incidence of blood transfusions in cardiac surgery have been reported to vary from 27% to 90%. Controlling and stopping bleeding early postoperatively seems important and this means that anticoagulation therapy can be started earlier; hereby reducing the risk of thromboembolic events on the ICU.

Contamination Intraoperatively

During operation there are several factors that contribute to contamination of the pericardial blood, by causing disturbances in the haemostatic balance: cardiopulmonary bypass (CPB) use, operation trauma and aortic cross clamping; all of which result in thrombin generation and an anti-thrombotic reaction. Tissue factor (TF) and factor VII are rapidly generated in pericardial blood during bypass. TF levels in the pericardial blood can increase to five fold above systemic levels [PPS7]. Systemic blood contact with TF within the pericardial cavity represents a significant trigger for the activation of the coagulation system [PPS1] and might result in a disseminated intravascular coagulation (DIC) state leading to excessive blood loss. Procedures with longer aortic cross-clamp times have been found to be associated with enhanced activation of t-PA during CPB]. Elevated active tissue plasminogen activator (t-PA) levels in the pericardial blood are associated with an increased rate of systemic fibrinolysis and therefore, also excessive bleeding. Re-transfusion of suctioned pericardial blood to the systemic circulation seems to reinforce: induction of pro-inflammatory markers, activation of leukocytes and platelets, activation of the complement system, increase of fibrinolytic cascade parameters and damage to red blood cells caused by CPB].

Contamination and Drain Obstruction

It is clear that during the first hours after cardiac surgery, clotting is suboptimal while a large internal wound remains. To evacuate blood from the pericardial-, and if necessary pleural cavities, the standard operating procedure is to leave chest tubes postoperative. The normal or generally accepted amount of blood loss after cardiac surgery varies between 300-1500 mL during the first 12 hours. However, when blood loss is excessive or when clots start to develop more rapidly, the drains often fail in their function to evacuate all accumulated blood. Stasis of blood and clots in the pericardial (and/or pleural) cavity leads to high fibrinolytic activity and maintenance of blood loss. This is confirmed by the observations made by cardiac surgeons, that during redo surgery for bleeding or tamponade, complete removal of blood and clots by flushing the pericardial cavity with warm saline is enough to stop the bleeding immediately in a vast majority of patients.

Contamination After Drain Removal

After removal of the chest tubes, often one day postoperatively, some blood and clots remain in the pericardial cavity. During the next days, under the influence of fibrinolysis and hemolysis, a highly osmotic liquid solution with high concentration of large molecular proteins (hemoglobin) is formed. This osmotic active solution is known to contribute to the increase of pericardial effusions and late cardiac tamponade in the first weeks postoperatively. Besides, it is also known that free blood outside the cardiovascular system produces inflammatory reactions in body cavities or tissues; peritonitis in the abdominal cavity or sterile pneumonitis in the lungs, etc. Blood and clots that remain in the pericardial cavity can therefor induce an inflammatory reaction that may play a role in the occurrence of postoperative supraventricular arrhythmias, the formation of adhesions and the decline of right ventricular function. Besides this, the blood remnants may be a causal link to postcardiotomy syndrome, of which the exact etiology is still not understood. Hematoma in general are known to be a rich culture medium for proliferation of bacteria and can therefore influence the incidence and severity of pericardial/mediastinal infections.

Thus, when not removed from the body, pericardial blood that is contaminated by tissue contact is a powerful stimulus for haemostatic activation (coagulation, DIC and fibrinolysis), inflammatory stimulation, and an important cause of excessive blood loss.

Complications

Transfusion Requirements

It has been pursued with the assumption that transfusing an anaemic patient will improve the outcome. Blood transfusion has a clearly defined role in the management of haemorrhagic shock and is presumably beneficial in situations where a critically low hematocrit is contributing to a state of oxygen-supply dependency. The potential benefits are, however, countered by many transfusion-associated complications: the risk of transfusion-associated lung injury, transfusion associated immunomodulation, transfusion-related circulatory overload, and cellular hypoxia. Blood transfusions have also been linked to postoperative renal dysfunction, pneumonia, wound infections and severe sepsis. There have been several recent well-designed randomized control trials in critically ill or CABG patients showing a significant association of transfusion with increased short- and long-term postoperative mortality of 66%; morbidity and healthcare costs. Different studies showed that lower Hb and Ht levels increase mortality as well. The short-term adverse effects of blood transfusion in cardiac surgical patients are well documented but there are few studies conducted assessing long-term survival. Others stated that bleeding, increased chest tube production, is associated with higher mortality through mechanisms not related to blood transfusion. Despite all the available evidence, the transfusion practices vary substantially. Efforts made to decrease transfusion rates in cardiac surgery show persistent effects for several years. The use of blood and other blood product transfusion in cardiac surgical patients still remains very high. Adult cardiac surgery utilizes a significant proportion of all packed red blood cell (PRBC) transfusions all over the world. The incidence of blood transfusion in patients undergoing cardiac surgery has been reported to vary from 27% to 90%.

Atrial Fibrillation

Besides directly causing patient discomfort and leading to hemodynamic compromise, several studies have demonstrated that post-operative atrial fibrillation (AF) is associated with: an increased risk of postoperative stroke, represented by an annual stroke rate of 5% in patients with AF; a higher rate of in-hospital mortality (5.8% vs. 2.2%, P=0.003); longer intensive care unit and hospital stays and higher costs of treatment. Both paroxysmal and chronic AF have shown a significant increase of the risk of stroke, especially in older patients.

Right Ventricular Function

CHD patients have a decline in right ventricular function directly after cardiac surgery, regardless the side of surgery and although a gradual improvement, complete recovery is not seen postoperatively. Various hypotheses regarding the pathogenesis of the selective decline in RVF after cardiac surgery have been put forward. However, no clear cause has been found. It is possible that the thin-walled right ventricle may be more susceptible to dysfunction secondary to inflammation or effusions postoperatively. These effusions may result from local tissue damage or from a systemic inflammatory response. Another theory suggests that postoperative pericardial adhesions may impair right ventricle filling. Prospective studies are needed to elucidate this phenomenon.

Pericardial Adhesions

The development of dense and tenacious adhesions can severely complicate re-operations by making re-entry hazardous, impeding orientation and visibility, prolonging operation time and it may result in prolonged bleeding and possible catastrophic haemorrhage. Additionally, pericardial adhesions may act to constrict the heart and restrict left ventricular diastolic filling, and there are data strongly indicating that adhesions comprise right ventricular contraction, causing postoperative right ventricular dysfunction. Taking down adhesions itself leads to an increase in surgical surface and trauma with an increased bleeding tendency an inflammatory reaction as a consequence, thereby creating a self-sustaining cycle of postoperative complications.

Hypothesis

We hypothesized that postoperative bleeding and stasis of blood in the pericardial space, hereby causing a soiled pericardial environment, could be a common determining factor for important postoperative complications such as: blood loss and related transfusion requirements, atrial fibrillation, postoperative right ventricular function impairment, cardiac effusions and tamponade and the formation of postoperative pericardial adhesions. The mechanisms involved in per- and postoperative bleeding however are complex and involve disturbances in various physiologic systems of the haemostatic balance including primary haemostasis, coagulation, and fibrinolysis.

CONCLUSIONS

Our findings support the technical feasibility and safety of our pericardial flushing system in patients undergoing cardiac surgery. The study population showed a significant reduction blood loss in comparison with a retrospective control group. Future large clinical trials to evaluate the effect on postoperative blood loss and transfusion requirements are needed. Two prospective randomized controlled clinical trials are currently being performed at our institution to provide final proof of concept.

The invention claimed is:

1. A flushing system configured to flush a pericardial cavity (PC) of a patient, wherein the system comprises:
    an infusion liquid outlet to connect a first tube having an infusion liquid lumen to guide a flow of infusion liquid from the system to the pericardial cavity,
    an effusion liquid inlet to connect to a second tube having an effusion liquid lumen to guide an effusion liquid flow from the pericardial cavity to the system, and
    a flow rate control system to control a flow rate of the infusion liquid flow at the infusion liquid outlet on the basis of multiple sensor signals, wherein the flow rate control system comprises:
        a control unit to provide a control signal on the basis of the sensor signals, and
        a pump device to pump infusion liquid to the infusion liquid outlet at an infusion liquid flow rate, wherein the infusion liquid flow rate is adjustable by the control signal of the control unit,
    and wherein the sensor signals registered by the control unit comprise:
        an infusion liquid signal representative for the infusion liquid flow to the pericardial cavity,
        an effusion liquid signal representative for the effusion liquid flow rate from the pericardial cavity,
        a blood volume signal generated by a hematocrit sensor representative for a blood loss flow rate in the effusion liquid from the pericardial cavity, and
        a pressure control signal representative for the pressure in the pericardial cavity generated by a pressure sensor positioned inside or in connection with the first tube, the second tube or the pericardial cavity.

2. The system of claim 1, wherein the flow rate control system is configured to control a ratio between the infusion liquid flow rate and the blood loss flow rate in the effusion liquid flow subject to control by the pressure sensor signal.

3. The system of claim 1, wherein the control unit is configured to determine a blood loss volume and/or blood loss volume rate from the pericardial cavity based on values generated by the hematocrit sensor.

4. The system of claim 1, wherein the first tube and the second tube are combined in an integrated outflow drain device.

5. The system of claim 1, wherein the system comprises an infusion liquid flow sensor to determine the flow rate of the infusion liquid flow, wherein said determined flow rate of the infusion liquid flow is used as the infusion liquid signal.

6. The system of claim 1, wherein the system comprises an effusion liquid flow sensor to determine a flow rate of the effusion liquid flow, and wherein the determined flow rate of the effusion liquid flow is used as the effusion liquid signal.

7. The system of claim 1, wherein the hematocrit sensor is configured to determine a value representative for the blood loss flow rate in the effusion liquid flow, and wherein the hematocrit value representative for the blood loss flow rate in the effusion liquid flow is used as the blood volume signal.

8. The system of claim 1, wherein the pressure control signal representative for the pressure in the pericardial cavity is generated by a pressure sensor which is part of a pressure control system to control the pressure in the pericardial cavity, comprising a pressure control unit to adjust the infusion liquid flow rate to keep the pressure control signal within desired pressure limits.

9. The system of claim 1, wherein the system comprises a heater device configured to heat the infusion liquid to a desired infusion liquid temperature.

10. The system of claim 1, wherein the system comprises a temperature control system to control a temperature of the infusion liquid flow, wherein the temperature control system comprises:
    a temperature sensor to measure a temperature of infusion liquid,
    a temperature control unit to provide a temperature control signal on the basis of the measured temperature of infusion liquid and a desired infusion liquid temperature, and a heater device, wherein the heater device is actuatable by the temperature control signal to heat the infusion liquid to the desired infusion liquid temperature.

11. The system of claim 10, wherein the desired temperature is based on a temperature of the pericardial cavity.

12. The system of claim 1, wherein the pump device is a volumetric pump.

13. The system of claim 1, wherein the system comprises one or more effusion liquid containers to receive effusion liquid from the pericardial cavity.

14. The system of claim 1, wherein the flushing system comprises one or more suction devices to draw effusion liquid out of the pericardial cavity.

15. The system of claim 1, wherein the second tube is provided with means to cause an automatic milking in case of occlusion.

16. A method of treatment of postoperative cardiac patients in order to reduce the risk of cardiac tamponade, reduce post-operative blood loss and reduce the accumulation of blood and clots in the pericardial cavity, wherein the pericardial cavity of the patient is flushed with a flushing system according to claim 1.

17. A method of monitoring a blood loss volume or a blood loss flow rate from a pericardial cavity of a patient by controlling a flow rate of an infusion liquid flow at an infusion liquid outlet on a basis of multiple sensor signals, which method comprises the following steps:
providing a signal from an infusion flow rate sensor indicating flow rate of infusion liquid to the pericardial cavity and registering this signal in a control unit,
providing a signal from an effusion flow rate sensor indicating flow rate of effusion liquid from the pericardial cavity and registering this signal in the control unit,
providing a signal from a hematocrit sensor indicating blood loss flow rate in effusion liquid from the pericardial cavity and registering this signal in the control unit, and
providing a signal from a pressure sensor indicating the pressure in the pericardial cavity in which the pressure sensor is positioned inside or in connection with a first tube, a second tube or the pericardial cavity and registering this signal in the control unit, and concomitantly or concurrently the control unit provides a control signal on the basis of the sensor signals, which control signal controls a pump device pumping infusion liquid to the infusion liquid outlet, the infusion liquid flow rate being adjustable by the control signal of the control unit.

18. The method of claim 17, wherein the signal indicating flow rate of effusion liquid from the pericardial cavity is provided from the effusion flow rate sensor being configured for registering increased volume in a container collecting effusion liquid.

19. The method of claim 17, wherein the infusion liquid is heated or cooled by a heater device, to a temperature in the range 36-38° C., which heater device is controlled either by the control unit, by an independent control unit or manually by medical or non-medical staff.

20. The method of claim 17, wherein the method further comprises the step of displaying, by a display device, the blood loss volume or blood loss flow rate from a body cavity.

21. The method of claim 17, wherein a display device displays instructions to involved medical or non-medical staff monitoring the patient.

* * * * *